United States Patent [19]

Duke

[11] 4,403,867
[45] Sep. 13, 1983

[54] INK AND WATER TESTER

[76] Inventor: Horace Duke, 1001 Massman Dr., Nashville, Tenn. 37217

[21] Appl. No.: 198,635

[22] Filed: Oct. 20, 1980

[51] Int. Cl.³ .............................................. B01F 15/00
[52] U.S. Cl. ............................ 366/142; 101/DIG. 8; 235/103; 366/199; 366/213; 366/224; 366/297; 366/601
[58] Field of Search ................. 366/56, 142, 200, 206, 366/213, 224, 232, 249, 251, 282, 199, 601, 297–301; 73/901; 235/103; 101/DIG. 8, DIG. 24

[56] References Cited

U.S. PATENT DOCUMENTS

| | | | |
|---|---|---|---|
| 3,582,969 | 6/1971 | Kinney | 235/103 |
| 4,076,220 | 2/1978 | Nakashima et al. | 366/601 |
| 4,166,705 | 9/1979 | Fronske | 366/224 |
| 4,176,971 | 12/1979 | Ernster et al. | 366/298 |

Primary Examiner—Philip R. Coe
Assistant Examiner—Timothy F. Simone
Attorney, Agent, or Firm—Pitts, Ruderman & Kesterson

[57] ABSTRACT

An emulsification tester for determining the amount of water a known amount of material such as printers ink or shellac will absorb when agitated or mixed a precise number of times and in a precise manner is disclosed. As is well known by those skilled in the art, certain materials, especially materials such as shellac and printers ink, will not function properly unless these materials have the ability to absorb a proper amount of water. That is, the material must be able to absorb a minimum amount of water but must not absorb an excess amount of water. The tester of this invention allows a precise amount of water and a material to be tested (such as printer ink) to be agitated by mixer blades rotating at a precise selected speed and for a precise number of revolutions. In addition, the tester of this machine further includes means for very positively but slowly rotating the container such that the mixer blades clearly come into contact with all portions of the material in the container and leaves none unagitated. Thus, as an example, the water absorption characteristics of printers ink can be determined after a precise amount of agitation simply by pouring off and measuring the remaining water. The apparatus comprises a heavy-duty mixer which uses a precise DC electric motor which in turn drives a gear box connected to the mixers or agitators such that the agitators rotate at a precise revolution per minute. The container itself is driven at a slow speed (approximately 4 RPM) by a small AC motor. A sensing means connected to one of the agitators or mixer blades senses each revolution of the blades. A pulse representative of each of these revolutions is then provided to a countdown counter which counts each pulse received from said pulsing means. Thus, when a selected number of turns is preset in the counting means, and the machine started, it will be appreciated that once the counter reaches zero, electrical power is interrupted to the DC motor and AC motors thereby stopping the agitation. A light indicator, buzzer or other audible device may be attached to give notice that the mixing is complete. At that time, the water can be poured off and measured to determine the amount absorbed.

6 Claims, 2 Drawing Figures

INK AND WATER TESTER

BACKGROUND OF THE INVENTION

The present invention relates to mixing apparatus in general and more particularly to an emulsification tester which precisely agitates a mixture of water and material such as printers ink or shellac to determine the ability of the material to absorb the water.

It will be appreciated that home and commercial mixers have been available for a long time. For example, U.S. Pat. No. 2,931,232 issued to E. Martin on Apr. 5, 1960 discloses a heavy-duty power commercial mixer having a variable speed transmission and a direct drive from an electrical motor. This mixer also uses a double acting rotating agitator or mixer blade. That is, the mixer blade not only rotates on its own axis but also rotates along a prescribed circular path. This prescribed circular path is for purposes of assuring the contact of the mixer blade or agitator with the mixing bowl itself. Thus, it is seen in this mixer that the mixing bowl is held stationary and cannot move.

There are, of course, specialty mixers such as the bread making mixer illustrated in U.S. Pat. No. 4,159,879 issued to Robert G. Coucher on July 3, 1979. This patent includes a high speed, low powered, electrical motor which is geared to a dough hook, and which moves at a slow rate of approximately 52-75 RPM for kneading bread dough. The mixer of Coucher, however, does not in any way include means for precisely determining the number of revolutions per minute and would not be suitable for purposes of testing the emulsification abilities of printers ink or shellac.

U.S. Pat. No. 4,091,463 issued to Roland Tschundy et al on May 23, 1978 illustrates a vat or bucket mixture for commingling liquid and powder components during the production of printing inks. According to this invention, a first mixing tool rotates about the first shaft within a container. At the same time a dissolver disk is rotated.

Thus, it can be seen that there are a plathora of mixing devices, both commercial and domestic, as well as mixers designed for specific purposes. In the printing industry it is of great importance to know the water abosorbing characteristics of printer ink paste prior to the paste being used. That is, proper printing and adhering to the paper cannot be achieved if the paste cannot absorb sufficient water. However, in a similar manner, proper adherence cannot be achieved if the ink has the ability to absorb too much water. Thus, printers ink must be able to absorb a precise amount of water for proper operation. To this end, emulsification testing has been accomplished by the use of commercially available home mixers which have been modified to turn at a slow rate of speed. These modified mixers, however, do not provide sufficient speed control, and require constant monitoring of the apparatus in an attept to determine the number of turns to help maintain consistency in the test. Unfortunately, use of the prior art apparatus and procedures require great experience and careful monitoring at all times. The apparatus described in the present invention, on the other hand, removes the guess work and allows precise measurements of the water absorption characteristics of the material without constant monitoring.

SUMMARY OF THE INVENTION

Therefore, it is an object of the present invention to provide a heavy-duty emulsification testing apparatus which can be pre-set and requires little or no monitoring.

It is a further object of this invention to provide apparatus which can continuously repeat testing conditions such that the water absorbing charateristics of the material can be determined.

Yet another object of this invention is to provide an emulsification tester which provides a precise amount of agitation and terminates the testing.

Briefly, the emulsification tester of this invention for testing the water absorption characteristics of selected materials comprises a container to which is added a selective quantity of the material to be tested such as water absorbent printers ink or shellac and a measured selected quantity of water. The container is supported by a base means in such a manner that the container may rotate. An agitator such as a pair of mixer blades is supported by an upper support such that the agitators or blades reach to the interior of the container in such a manner that the water absorbing material and water may be thoroughly agitated. The device further includes a driving means such as an AC motor for rotating the container and a second driving means for driving the agitator means at a precise speed. Also included is a means for determining the number of revolutions of the agitator means for controlling circuitry which can interrupt the electrical power to the drive means. Thus, by presetting the counter, a mixture containing a precise quantity of water and a selected material can be agitated precisely such that the absorption characteristics of the material can be determined.

A particular embodiment of the machine uses a powerful DC motor which is connected to the agitators by gearing means for reducing the speed to a selected rate. In addition, a sensor monitors each revolution of the agitator and in turn steps the counter such that a precise count can be maintained.

DESCRIPTION OF THE INVENTION

Figure 1:
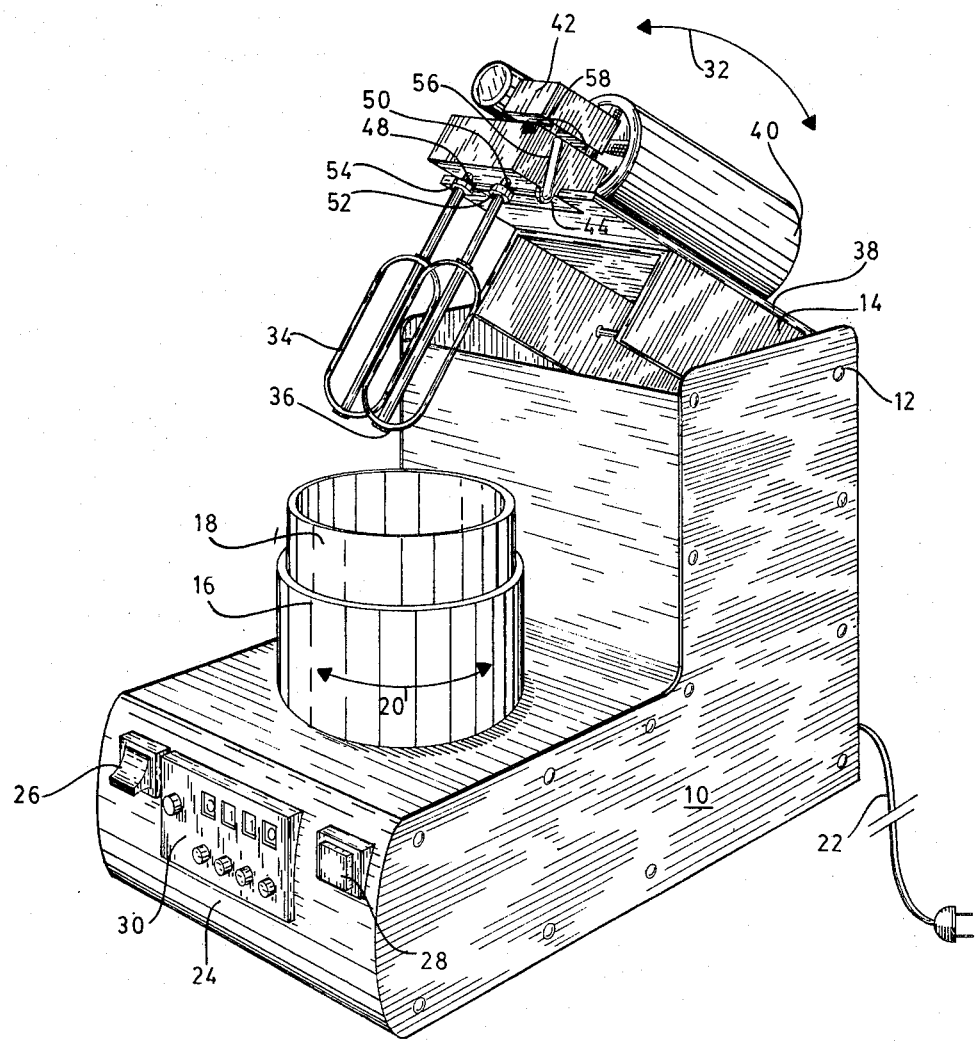
FIG. 1 is a perspective view of the emulsification tester of this invention showing the agitators rotated out of the specimen container.

Referring now to FIG. 1, there is shown a perspective view of the emulsification tester of this invention. As shown, there is a L-shaped base support structure 10 to which there is pivotally attached at 12 a upper support structure 14. Base supprt structure 10 includes a rotating support member 16 suitable for holding specimen cup 18. Member 16 is rotatably attached at a pivot point (not shown) so that it can rotate in the directions as illustrated by arrow 20. A standard 110 electrical AC power line and plug 22 supplies power to the system by means of base support 10. A control panel 24 at the front of base support 10 includes an on and off power switch 26, a power on indicating light 28 and a resetable revolution counter 30, which which will be discussed in detail hereinafter.

As can be seen, upper support member 14 pivots at pivot point 12 with respect to base support 10 such that the support member may tilt or rotate in the directions indicated by arrow 32. Pivoting of upper support member 14 is provided so that mixer blades or agitators 34 and 36 may be lowered into the interior of specimen cup 18 when the apparatus of this invention is in operation or may be rotated or tilted out of the way such that specimen cup 18 may be removed. As shown, support member 14 includes a flat plate 38 to which there is attached an electrical drive motor 40. It will be appreciated that electrical drive motor 40 may comprise any suitable drive motor but is preferably a 1725 RPM, DC motor. Attached to the shaft (not shown) of drive motor 40 is a gearing box 42 by means of which the shaft of drive motor 40 is connected to the mixer blades or agitators 34 and 36. As will be discussed hereinafter, the rotational speed of mixer blade 34 and 36 is substantially reduced by the gearing in the gear box 42. Although suitable gearing resulting in any selected mixer blade speed may be provided, it will be appreciated that for purposes of using the tester of this invention for a material such as printers ink paste and shellac, the resulting speed of meters 34 and 36 has been found to be especially effective at approximately 90 RPM. A mixer blade engaging member 44 is rotatably attached to the underside 46 of plate 38 such that fingers 48 and 50 will bear against collars 52 and 54 to eject mixer blades 34 and 36 when lever arm 56 is rotated in the direction shown by arrow 58. Thus, there has been described in general terms to this point, an ink emulsification tester having the ability to provide precise agitation to a selected amount of water absorbent materials such as printers ink and shellac and a selected amount of water so that the water absorption characteristics of the material can be determined.

Figure 2:
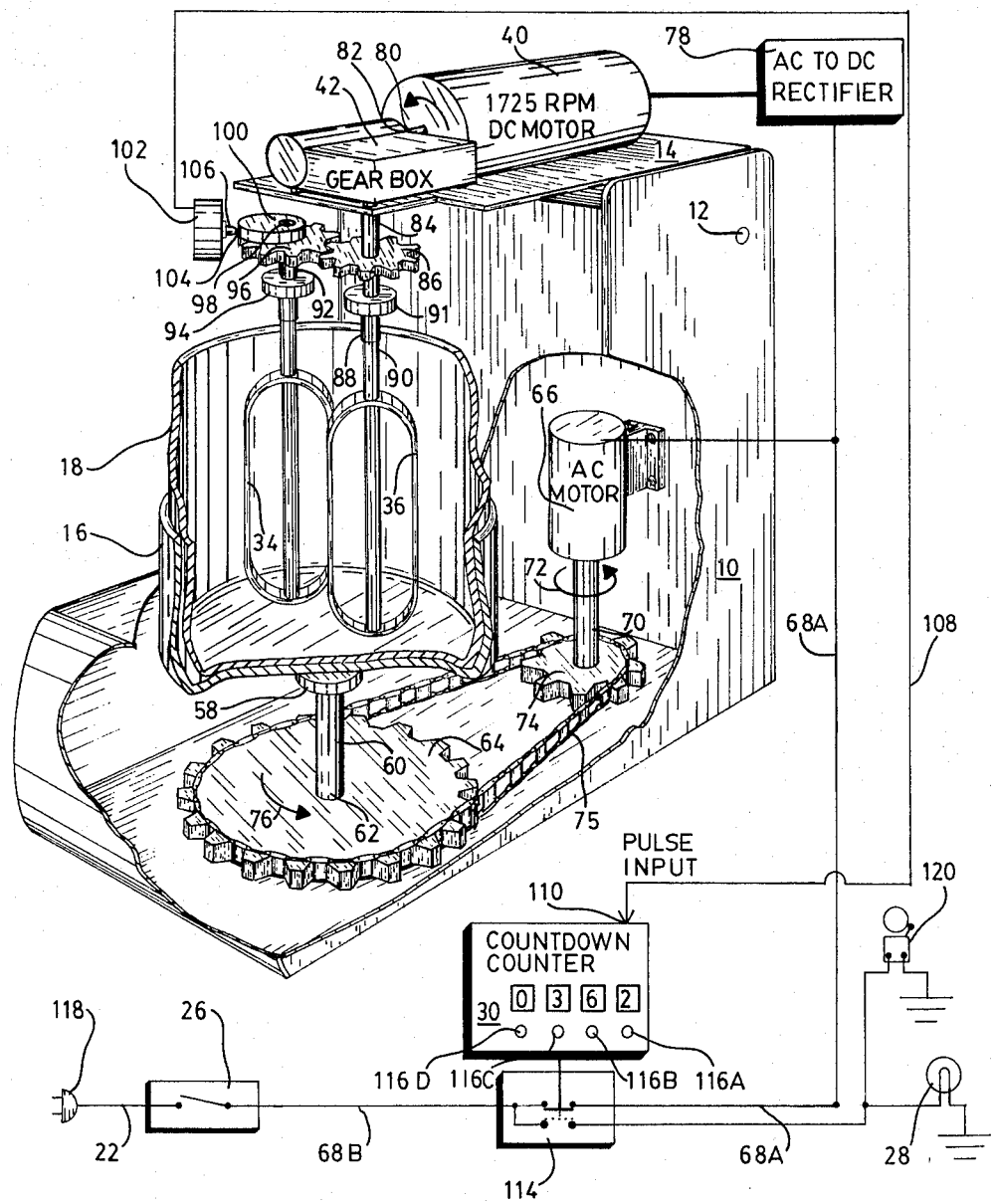
FIG. 2 is a part schematic, part block diagram showing the various features and details of the present emulsification tester of this invention.

Referring now to FIG. 2, there is shown a partial schematic, partial block diagram of the ink emulsification mixer tester of this invention. For those components of FIG. 2 which are common with the components with respect to FIG. 1, the same reference numerals have been used. Thus, as shown, base support 10 pivotally supports rotating member 16 which is held in place by means of bearing 58 through which passes shaft 60. The lower end 62 of shaft 60 is attached to the axis of rotation of spur gear 64. An AC motor 66 powered by standard AC 110 V, electrical power through line 68 provides rotation to shaft 70 in a selected direction such as that indicated by arrow 72. The lower end of shaft 70 is attached to a second spur gear 74. As can be seen, the diameter of spur gear 74 is substantially smaller than the diameter of spur gear 64. A timing belt drive 75 between the small spur gear 74 and large spur gear 64 imparts rotational motion to spur gear 64 in a direction indicated by arrow 76. It will also be appreciated that other connecting drive means such as a drive chain could be used. The rotation of spur gear 64 in turn imparts the rotation to rotating support member 16 and to specimen cup 18. As will be appreciated, the diameters of spur gear 74 and 64 may be selected such that cup 16 will rotate at any desired number of revolutions. However, it has been found particularly effective that specimen cup 18 rotate at a very slow speed such as example about 4 revolutions per minute. In addition to providing AC power to AC motor 66, power lines 68 also provides power to an AC/DC rectifier 78. AC/DC rectifier then provides DC power to DC motor 40. An AC motor could also be used, and thereby eliminate the need of AC/DC rectifier 78. The output shaft 80 of DC motor 40 is then provided to an input 82 of gear box 42.

Although not shown, gear box 42 may include any suitable type of gearing mechanism including worm type gearing. It will be appreciated, however, that if DC motor 40 is selected to be a 1725 RPM motor, and if it is desirable that mixer blade 34 and 36 rotate at 90 RPM, gear box 42 must provide this reduction of rotational speed. As shown, gear box 42 provides an output by means of shaft 84 which in turn drives a spur gear 86. Bottom portion 88 of drive shaft 84 receive end 90 of agitator or mixer blade 36. Bearing 91 provides rotational support for shaft 88. Mixer blade 34 which meshes with mixer blade 36, is itself rotatably supported on shaft member 92 by means of bearing 94. Rotational shaft 92 includes a spur gear 96 which engages spur gear 86 and which is of the same size and has the same number of teeth. Upper end 98 of shaft 92 includes a cam member 100. A sensing means 102 is located adjacent cam 100 to sense each rotation of said mixer blade 34. In the embodiment shown sensing means 102 is simply a micro switch. Thus, in operation rotation of cam 100 causes lobe 104 of cam 100 to activate pushbutton 106 of sensing means 102. Each time lobe 104 activates button 106 of microswitch 102, an electrical pulse is provided by means of electrical line 108 to an input point 110 of countdown counter 30. As shown, countdown counter 30 is connected to a switch 112 for interrupting electrical power. In the embodiment shown, countdown counter 12 simply opens and closes the contacts 114 of switch 112. Thus, in operation, a selected number or count is dialed into the countdown counter such as shown in the figure. As shown, for example, a number 362 has been dialed into the countdown counter by means of selection buttons 116 A, B, C, and D. In operation, contacts 114 are maintained in a closed position so long as countdown counter 30 is not all zero's. Each pulse received by countdown 30 decrements the number set in windows 116 A, B, C, and D, and therefore as the rotation of beaters 34 progresses the number displayed decreases. Upon the number in display 116 A, B, C, and D changing to all zero's, contacts 114 opened. Thus, any power available on line 68B, and passing through contacts 114 to line 68A is interrupted. Also as is shown, the apparatus of this invention preferably operates on commercial AC 110 volt power. Thus, there is shown plug 118 which provides power to an on and off switch 26. When switch 26 is closed, the power can pass through switch 26 along line 68B through contacts 114 to line 68A and then to motor 66 and AC to DC rectifier 78. Also in the embodiment shown, when power is supplied on line 68A, power lamp 28 will be illuminated. It may also be desireable to include an addition to power indicator 28. For example, some sort of audible alarm 120 such as a buzzer or bell may be provided.

In operation, therefore, it will be appreciated that to use the present apparatus as an ink and water emulsification tester, the following procedure is suggested. A known amount of printers ink paste and a known amount of water are placed in specimen cup 18. A selected number of turns for beaters 34 and 36 is dialed into countdown counter 30. Since countdown counter 30 is not zero, contacts 114 will be closed. Power switch 26 is then turned on which in turn activates AC motor 66 and provides power to DC motor 40 through AC/DC rectifier 78. Thus, support member 16 starts rotating as it is driven by spur gear 64 at a selected RPM such as 4 revolutions per minute. Concurrently, mixture blades 34 and 36 start rotating at their selected speed which is preferably at about 90 revolutions per minute. Mixing or agitation continues until the lobe 104 of cam 100 has pulsed microswitch 102 a number of times equivalent to that dialed in the countdown counter 30. At that time, countdown counter 30 will have been decremented or stepped to zero. Upon being decremented to zero, countdown counter 30 opens contacts 114 of switch 112 such that power is no longer provided to AC motor 66 and AC/DC rectifier 78. The removal of power on 68A also cuts off power indicator light 28 and sets off audible alarm 120 such that the operator is aware that a precise amount of agitation has been provided to the ink paste, and water mixture. The specimen cup 18 is then removed from the apparatus and the water standing on top of the ink paste is poured off and measured. The amount of water remaining is used to determine the amount of water absorbed by the ink. This information is then used to calculate the absorption characteristics of the ink.

Therefore, it will be appreciated that there has been described to this point an apparatus for testing the absorption characteristics of material such as printers ink and shellac. Further, the present invention has been described with respect to specific embodiments, and it is not intended that such specific references be considered as limitations of the scope of this invention except insofar as set forth in the following claims.

I claim:

1. Apparatus for testing the water absorption ability of a material comprising:
    container means suitable for rotating, and receiving a selected quantity of water absorbent material and a selected quantity of water;
    a base support suitable for rotating and supporting said container means;
    rotating agitator means suitable for being received by said container and for mixing and agitating said water absorbing material and water;
    an upper support for rotatably supporting said agitator means, said upper support being mounted to said base support such that said agitator means is positioned within said container means at a position suitable for mixing and agitating said water absorbent material and water;
    first drive means supported by said upper support for rotating said agitator means at a first selected rate;
    means for counting the number of revolutions of said agitator means;
    second drive means supported by said base support for rotating said container means at a second selected rate to assure said agitator means contacts all said water absorbent material in said container means; and
    circuitry connected to said means for counting, for interrupting electrical power to said first drive means when said agitator has completed a selected number of revolutions.

2. The testing apparatus of claim 1 wherein said agitator means is a pair of mixer blades.

3. The testing apparatus of claim 1 where in said first drive means comprises means for converting AC power to DC power, a DC motor which rotates at a selected speed, and gearing means connected between said DC motor and said agitator means for providing a reduced rotating speed to said agitator means such that said agitator means rotates at said selected speed.

4. The testing apparatus of claim 1 wherein said upper support is pivotally mounted on said base support such that said agitator means may be removed from said container means by upwardly pivoting said upper support.

5. The testing apparatus of claims 1, 3, or 4 wherein said container means includes a pulsing means for providing an electrical pulse for each revolution of said agitator means, a counter for counting each of said electrical pulses, and dial means for presetting the number of revolutions desired for each operation of said apparatus.

6. The testing apparatus of claim 5 wherein said second drive means comprises an AC motor, and connecting means between said AC motor and said container means for rotating said container means.

* * * * *